(12) United States Patent
Yan

(10) Patent No.: US 7,868,110 B2
(45) Date of Patent: Jan. 11, 2011

(54) ANIONIC POLYMERIZATION INITIATORS AND POLYMERS THEREFROM

(75) Inventor: Yuan-Yong Yan, Copley, OH (US)

(73) Assignee: Bridgestone Corporation (JP)

( * ) Notice: Subject to any disclaimer, the term of this patent is extended or adjusted under 35 U.S.C. 154(b) by 917 days.

(21) Appl. No.: 11/435,613

(22) Filed: May 17, 2006

(65) Prior Publication Data

US 2006/0264589 A1 Nov. 23, 2006

Related U.S. Application Data

(60) Provisional application No. 60/683,231, filed on May 20, 2005.

(51) Int. Cl.
*C08F 4/00* (2006.01)
*C07D 409/02* (2006.01)

(52) U.S. Cl. ..................... 526/217; 544/374
(58) Field of Classification Search ............. 526/217, 526/335, 222; 544/145, 105, 374
See application file for complete search history.

(56) References Cited

U.S. PATENT DOCUMENTS

| | | | | |
|---|---|---|---|---|
| 3,699,191 | A | 10/1972 | Niemann | 260/881 |
| 4,429,091 | A | 1/1984 | Hall | 526/181 |
| 4,519,430 | A | 5/1985 | Ahmad et al. | 152/209 |
| 4,616,069 | A | 10/1986 | Watanabe et al. | 525/370 |
| 5,496,940 | A | 3/1996 | Lawson et al. | 540/450 |
| 5,502,131 | A | 3/1996 | Antkowiak et al. | 526/180 |
| 6,053,226 | A | 4/2000 | Agostini | 152/209.5 |
| 6,476,143 | B2 | 11/2002 | Lawson et al. | 525/194 |
| 6,518,335 | B2 | 2/2003 | Reedy et al. | 524/82 |
| 6,720,391 | B2 | 4/2004 | Schwindeman et al. | 525/355 |
| 7,153,919 | B2 | 12/2006 | Hogan et al. | 526/335 |
| 2006/0074197 | A1 | 4/2006 | Hogan et al. | 525/331.9 |
| 2006/0264590 | A1 | 11/2006 | Hogan et al. | 526/222 |

FOREIGN PATENT DOCUMENTS

| EP | 709408 | 1/2001 |
|---|---|---|
| WO | 04/041870 | 5/2004 |

OTHER PUBLICATIONS

"*Highly Regioselective Additions of Certain 2-lithio-1,3-dithianes to Conjugated Ketones*," by Ostrowski et al., Tetrahedron Lett., pp. 3549-3552 (1977).

"*Trends in the Chemistry of 1, 3-Dithioacetals*," by Wood, Organosulfur Chemistry, pp. 133-224 (1995).

"*Anionic Living Polymerization of Useful Monomers that can provide Intermolecular Chemical Links*" by Kazunori Se, Prog. Polymer. Sci, pp. 583-618 (2003).

"*Recent Advance in Living Anionic Polymerization of Functionalized Styrene Derivatives*" by Hirao et al., Prog. Polymer Sci., pp. 1399-1471, (2002).

"*Polymerization of Vinyl Monomers by Alkali Metal-Thiobenzophenone Complexes*",Yuji Minoura and Sadao Tsuboi, Journal of Polymer Science: Part A-1 vol. 8, 125-138 (1970).

"*A Convenient High Yield Synthesis of Functional Methacrylates via Dethioacetalization. Synthesis of Methacrylate S,S-Acetal Derivatives as Intermediates*", Florence Caye et al., Phosphorus, Sulfur and Silicon, vol. 143, 197-220 (1998).

"*Organosulfur Chemistry. 3. NMR Spectra of Carbanions Derived from 1, 3-Dithianes as Related to the High Stereoselectivity in their Reactions with Electrophiles*", Anthony G. Abatjoglou et al., Journal of the American Chemical Society, Dec. 7, 1977.

"*Synthesis of Symmetrical and Unsymmetrical 2,5-Bis(trialkylsilyl)furans and 2,6-Bis(trialkylsilyl)-4H-pyrans from 1,4- and 1,5-Bis(acylsilanes)*", Jean-Philippe Bouillon et al., Synthesis 2000, No. 6, 843- 849, Sep. 26,1999.

"*Protonation and Methylation of Conformationally Fixed 2-Lithio-1, 3-dithianes. Some Reactions of Remarkable Stereoselectivity*", A. A. Hartman et al., Journal of the American Chemical Society, vol. 93, 2572-3 (1971).

*Primary Examiner*—Kamal A Saeed
*Assistant Examiner*—Kristin Bianchi
(74) *Attorney, Agent, or Firm*—Meredith E. Hooker; Arthur Reginelli

(57) ABSTRACT

An initiator compound comprising an aryl or heteroaryl thioacetal including a substituent defined by the formula

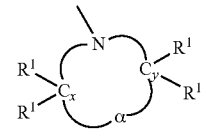

where x is an integer from 1 to about 5, y is an integer from 1 to about 5, the sum of x and y is from about 3 to about 6, $\alpha$ is carbon, sulfur, oxygen, silicon, or an amino group, and each $R^1$ is individually hydrogen or a monovalent organic group or where two or more $R^1$ groups may join to form one or more rings.

19 Claims, No Drawings

ANIONIC POLYMERIZATION INITIATORS AND POLYMERS THEREFROM

This application claims the benefit of U.S. Provisional Application No. 60/683,231, filed May 20, 2005, which is incorporated herein by reference.

FIELD OF THE INVENTION

One or more embodiments of this invention are directed toward compounds that are useful as anionic polymerization initiators.

BACKGROUND OF THE INVENTION

Anionic polymerization techniques have been used to synthesize polymers that are useful in the manufacture of tires. Certain initiators impart a functional group to the polymer, and these functional groups are believed to have a beneficial impact on the performance of tires.

The synthesis of polymers by anionic polymerization is often advantageously conducted in non-polar organic solvent. It is therefore desirable that the initiator compounds bearing the functional groups exhibit some useful degree of solubility in these solvents. In particular, it is highly desirable to employ aliphatic solvents such as technical hexanes, and therefore initiator compounds that exhibit useful solubility in these solvents are likewise highly advantageous.

Unfortunately, inasmuch functional initiators often include metallated organic ligands that include one or more hetero atoms, the solubility of these compounds in solvents, particularly aliphatic solvents, is limited. Moreover, the ability to predict which compounds are soluble in aliphatic solvents is extremely difficult inasmuch as the metallation of the organic species often alters the solubility characteristics.

Because functional initiators remain desirable, particularly for the synthesis for functionalized polymers that are used in the manufacture of tires, there is a continued desire to identify initiators that can lead to technologically useful polymers and that exhibit a technologically useful solubility in aliphatic solvents in order to facilitate the polymerization process.

SUMMARY OF THE INVENTION

In general the present invention provides an initiator compound comprising an aryl or heteroaryl thioacetal including a substituent defined by the formula

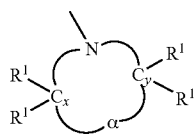

where x is an integer from 1 to about 5, y is an integer from 1 to about 5, the sum of x and y is from about 3 to about 6, α is carbon, sulfur, oxygen, silicon, or an amino group, and each $R^1$ is individually hydrogen or a monovalent organic group or where two or more $R^1$ groups may join to form one or more rings.

The present invention further comprises a composition comprising an initiator compound including an aryl or heteroaryl thioacetal including a substituent defined by the formula

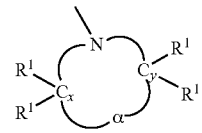

where x is an integer from 1 to about 5, y is an integer from 1 to about 5, the sum of x and y is from about 3 to about 6, α is carbon, sulfur, oxygen, silicon, or an amino group, and each $R^1$ is individually hydrogen or a monovalent organic group or where two or more $R^1$ groups may join to form one or more rings; and a solvent, where the composition includes at least 0.3 molar initiator compound and the solvent includes at least 65 volume percent aliphatic or cycloaliphatic solvent.

The present invention still further includes a method of preparing a polymer by employing anionic polymerization techniques, the method comprising (i) providing monomer including conjugated dienes; (ii) a polymerization and medium including a non-polar solvent; (iii) providing an initiator solution including an aryl or heteroaryl thioacetal including a substituent defined by the formula

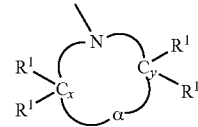

where x is an integer from 1 to about 5, y is an integer from 1 to about 5, the sum of x and y is from about 3 to about 6, α is carbon, sulfur, oxygen, silicon, or an amino group, and each $R^1$ is individually hydrogen or a monovalent organic group or where two or more $R^1$ groups may join to form one or more rings; and (iv) contacting the monomer and initiator within the polymerization medium.

One or more embodiments of the present invention also provides a functionalized polymer defined by the formula

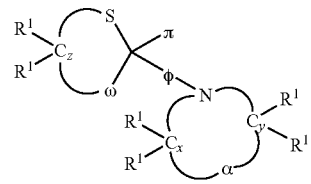

where φ includes an aryl or heteroaryl substituent, x is an integer from 1 to about 5, y is an integer from 1 to about 5, the sum of x and y is from about 3 to about 6, α is carbon, sulfur, oxygen, silicon, or an amino group, π is a polymer chain, and each $R^1$ is individually hydrogen or a monovalent organic group or where two or more $R^1$ groups may join to form one or more rings.

DETAILED DESCRIPTION OF ILLUSTRATIVE EMBODIMENTS

One or more embodiments of the invention include initiator compounds that are useful for anionically polymerizing monomer including conjugated diene monomer. In one or more embodiments, these compounds may be characterized by an increased solubility in solvents that include aliphatic or cycloaliphatic solvents. This increased solubility in aliphatic or cycloaliphatic solvents is believed to result from a solubilizing component present within the compound. In one or more embodiments, the solubilizing substituent may also interact with filler compounds and thereby improve certain properties of cured rubber compositions.

In one or more embodiments, the initiator compounds include lithiated aryl or heteroaryl thioacetals that include a solubilizing substituent. In general, lithiated aryl thioacetals are disclosed in International Application No. WO 2004/041870, which is incorporated herein by reference. Lithiated aryl and heteroaryl thioacetals include those compounds defined by the formula

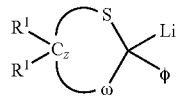

where ω is sulfur, oxygen, or tertiary amino (NR, where R is a monovalent organic group), φ is an aryl or heteroaryl substituent, each $R^1$ is independently hydrogen or a monovalent organic group, and z is an integer from 2 to about 8.

For example, lithiated aryl and heteroaryl dithianes include those compounds defined by the formula

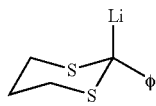

where φ includes an aryl or heteroaryl substituent.

Exemplary aryl or heteroaryl substituents include phenyl, thiophenyl, furanyl, N-methylpyrrolyl, thiazolyl, and pyridinyl groups.

The solubilizing substituent can be defined by the formula

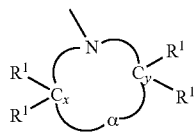

where x is an integer from 1 to about 5, y is an integer from 1 to about 5, the sum of x and y is from about 3 to about 6, α is carbon (C), sulfur (S), oxygen (O), silicon (Si), or an amino group (NR, where R is an organic group), and each $R^1$ is individually hydrogen or a monovalent organic group or where two or more $R^1$ groups may join to form one or more rings.

In one or more embodiments, the solubilizing substituent can be attached to the aryl or heteroaryl substituent of the thioacetal. Where the aryl substituent is a phenyl substituent, the solubilizing substituent may be positioned in the ortho, meta, or para position of the phenyl substituent.

Useful solubilizing substituents include imidazolyl, pyrazolyl, pyrazolidinyl, 1,2,3-triazolyl, piperidinyl, morpholinyl, thiomorpholinyl, piperazinyl, indolyl, isoindolyl, indolinyl, benzimidazolyl, 1H-indazolyl, purinyl, carbazolyl, phenothiazinyl, and phenoxazinyl groups.

In one or more embodiments, the lithiated aryl or heteroaryl thioacetals include those defined by the formula

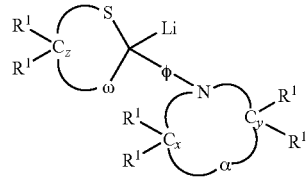

where each $R^1$, ω, α, φ, x, y, and z are defined as above. For example, in one or more embodiments, lithiated aryl or heteroaryl dithianes include those defined by the formula

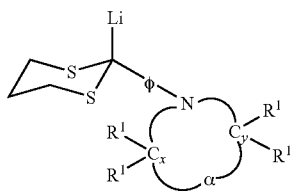

where φ, x, y, and $R^1$ are defined as described above.

Examples of useful initiator compounds of this invention include 2-lithio-[4-(4-methylpiperazino)]phenyl-1,3-dithiane, 2-lithio-[2-(4-methylpiperazino)]phenyl-1,3-dithiane, 2-lithio-[2-morpholino]phenyl-1,3-dithiane, 2-lithio [4-morpholin-4-yl]phenyl-1,3-dithiane, 2-lithio-[2-morpholin-4-yl-pyridine-3]-1,3-dithiane, 2-lithio-[6-morpholin-4-pyridino-3]-1,3-dithiane, 2-lithio-[4-methyl-3,4-dihydro-2H-1,4-benzoxazine-7]-1,3-dithiane, and mixtures thereof.

In one or more embodiments, the solubilizing substituent advantageously may provide greater functionality to the polymer. As a result, these polymers may be used to prepare cured rubber compositions that are characterized by advantageous viscoelastic properties including reduced loss of mechanical energy to heat (i.e., hysteresis loss at certain temperatures).

In one or more embodiments, the initiator solutions of this invention include one or more of the initiator compounds defined above and a solvent that includes an aliphatic or cycloaliphatic solvent. These initiator solutions may be useful for preparing, storing, using, transporting, or delivering the initiator compounds of this invention. Some representative examples of suitable aliphatic solvents include n-pentane, n-hexane, n-heptane, n-octane, n-nonane, n-decane, isopentane, isohexanes, isoheptanes, isooctanes, 2,2-dimethylbutane, petroleum ether, kerosene, petroleum spirits, and mixtures thereof. Some representative examples of suitable cycloaliphatic solvents include cyclopentane, cyclohexane, methylcyclopentane, methylcyclohexane, and mixtures thereof. Mixtures of aliphatic and cycloaliphatic solvents may be employed.

In one or more embodiments, the solvent employed in the initiator solutions may also include an ether solvent. Useful ethers include tetrahydrofurane (THF), 1,2-dimethoxyethene, 1,6-dimethoxyhexane, 1,3-dioxane, 1,4-dioxane, anisole, ethoxybenzene, and mixtures thereof.

The mixtures of aliphatic or cycloaliphatic solvents and ether solvents may include up to about 65 volume percent aliphatic or cycloaliphatic solvent, in other embodiments up to about 55 volume percent aliphatic or cycloaliphatic solvents, or in other embodiments up to about 45% aliphatic or cycloaliphatic solvent, with the remainder including an ether; in these or other embodiments, the mixtures of aliphatic or cycloaliphatic solvents and ether solvents include at least 10 volume percent, in other embodiments at least 20 volume percent, in other embodiments at least 30 volume percent, and in other embodiments at least 40 volume percent aliphatic or cycloaliphatic solvent.

In one or more embodiments, the initiator solutions of this invention may include 0.6 molar initiator solutions including up to about 30 volume percent aliphatic or cycloaliphatic solvent, where the initiator compound is soluble and stable at room temperature and standard pressure for 24 hours. In other embodiments, initiator solutions may include 0.3 molar initiator solutions including up to about 65 volume percent, and in other embodiments up to about 70 volume percent aliphatic or cycloaliphatic solvent, where the initiator compound is soluble and stable at room temperature and standard pressure for 24 hours.

The initiator compounds of this invention can be prepared by several synthetic routes. For example, WO 2004/041870, which in incorporated herein by reference, discloses methods for preparing dithiane compounds, as well as methods for lithiating dithiane compounds. In one or more embodiments, the thioacetals can be formed by reacting an aldehyde with 1,3-propanedithiol. These reactions may take place in the presence of a catalyst such as a Bronsted or Lewis acid.

In one or more embodiments, a dithiane compound bearing the solubilizing substituent can be reacted with an organolithium compound (e.g., n-butyllithium) to provide the lithiated thioacetal. The reaction may optionally take place in the presence of a stabilizer such as triethylamine. The stabilizer may assist in preventing the formation of lithium hydride. The lithiation reaction may occur at standard conditions within a solvent. The solvent may include a polar solvent, a non-polar solvent, or a mixture of polar and non-polar solvents. Where mixtures of polar and non-polar solvents are employed, the mixture may be similar to those described above with respect to the initiator solutions.

In one or more embodiments, the lithiated species may be prepared in situ (i.e., in the presence of the monomer to be polymerized) or in advance of contacting the initiator with the monomer to be polymerized. When prepared in advance, the lithiated species may be directly employed in the polymerization reaction by delivering the lithiated species to the monomer immediately or within a short period of time (e.g., less than 5 minutes). In other embodiments, the lithiated species may be stored prior to use in the polymerization reaction period. In one or more embodiments, the initiator solution can be stored at a temperature from about −25 to about 25° C., or in other embodiments from about −10 to about +10° C. for at least one week, or in other embodiments at least two weeks. In yet other embodiments, the lithiation reaction can take place in the presence of a small amount of monomer (e.g., 1 to about 100 mole per mole of lithium), and then this solution can be subsequently contacted with the remainder of the monomer to be polymerized.

The initiator compounds of this invention can be used to polymerize monomer including conjugated dienes according to conventional anionic polymerization techniques. In general, these processes include combining, introducing, or contacting the initiator compound with monomer. This may take place in the presence of a solvent. The process results in a living polymer that can be protonated or further functionalized.

Monomer that can be polymerized by the initiator compounds of the present invention include any monomer capable of being polymerized according to anionic polymerization techniques. These monomers include those that lead to the formation of elastomeric homopolymers or copolymers. Suitable monomers include, without limitation, conjugated $C_4$-$C_{12}$ dienes (optionally together with $C_8$-$C_{18}$ monovinyl aromatic monomers) and $C_6$-$C_{20}$ trienes. Examples of conjugated diene monomers include, without limitation, 1,3-butadiene, isoprene, 1,3-pentadiene, 2,3-dimethyl-1,3-butadiene, and 1,3-hexadiene. A non-limiting example of trienes includes myrcene. Aromatic vinyl monomers include, without limitation, styrene, α-methyl styrene, p-methylstyrene, and vinylnaphthalene. When preparing elastomeric copolymers, such as those containing conjugated diene monomers and aromatic vinyl monomers, the conjugated diene monomers and aromatic vinyl monomers are normally used at a ratio of 95:5 to 50:50, and preferably 95:5 to 65:35.

The amount of initiator employed in conducting anionic polymerizations can vary widely based upon the desired polymer characteristics. In one or more embodiments, from about 0.1 to about 100, in other embodiments from about 0.33 to about 10, and in other embodiments from about 0.2 to 1.0 mmol of lithium per 100 g of monomer is employed.

The polymerization processes of this invention may be conducted in non-polar solvents and mixtures of non-polar solvents with polar-solvents including those discussed above. In order to promote randomization in copolymerization and to control vinyl content, a polar coordinator may be added to the polymerization ingredients. Amounts may range between 0 and 90 or more equivalents per equivalent of lithium. The amount may depend on the amount of vinyl desired, the level of styrene employed and the temperature of the polymerization, as well as the nature of the specific polar coordinator (modifier) employed. Suitable polymerization modifiers include ethers or amines to provide the desired microstructure and randomization of the comonomer units.

Compounds useful as polar coordinators include those having an oxygen or nitrogen heteroatom and a non-bonded pair of electrons. Examples include dialkyl ethers of mono and oligo alkylene glycols; "crown" ethers; tertiary amines such as tetramethylethylene diamine (TMEDA); linear THF oligomers; and the like. Specific examples of compounds useful as polar coordinators include tetrahydroftiran (THF), linear and cyclic oligomeric oxolanyl alkanes such as 2,2-bis (2'-tetrahydrofuryl)propane, di-piperidyl ethane, dipiperidyl methane, hexamethylphosphoramide, N—N'-dimethylpiperazine, diazabicyclooctane, dimethyl ether, diethyl ether, tributylamine and the like. The linear and cyclic oligomeric oxolanyl alkane modifiers are described in U.S. Pat. No. 4,429,091, incorporated herein by reference.

By reacting anionic initiators according to this reaction with certain unsaturated monomers, a living polymer is propagated into a polymeric structure. Throughout formation and propagation of the polymer, the polymeric structure may be anionic and "living." A new batch of monomer subsequently added to the reaction can add to the living ends of the existing chains and increase the degree of polymerization. A living polymer, therefore, includes a polymeric segment having a living or reactive end. Anionic polymerization is further described in George Odian, *Principles of Polymerization*, ch. 5 ($3^{rd}$ Ed. 1991), or Panek 94 J. Am. Chem. Soc., 8768 (1972), which are incorporated herein by reference.

Anionically polymerized living polymers can be prepared by either batch or continuous methods. A batch polymerization is begun by charging a blend of monomer(s) and normal alkane solvent to a suitable reaction vessel, followed by the addition of the polar coordinator (if employed) and an initiator compound. The reactants may be heated to a temperature of from about 20 to about 130° C. and the polymerization may be allowed to proceed for from about 0.1 to about 24 hours. This reaction produces a reactive polymer having a reactive or living end. In one or more embodiments, at least about 30% of the polymer molecules contain a living end, in other embodiments at least about 50% of the polymer molecules contain a living end, and in other embodiments at least about 80% contain a living end.

The living polymer can be protonated or subsequently functionalized or coupled. Protonation can occur by the addition of any compound that can donate a proton to the living end. Examples include water, isopropyl alcohol, and methyl alcohol.

In other embodiments, the living polymer can be terminated with a compound that will impart a functional group to the terminus of the polymer. Useful functionalizing agents include those conventionally employed in the art. Types of compounds that have been used to end-functionalize living polymers include carbon dioxide, benzophenones, benzaldehydes, imidazolidones, pyrolidinones, carbodiimides, ureas, isocyanates, and Schiff bases including those disclosed in U.S. Pat. Nos. 3,109,871, 3,135,716, 5,332,810, 5,109,907, 5,210,145, 5,227,431, 5,329,005, 5,935,893, which are incorporated herein by reference. Specific examples include trialkyltin halides such as triisobutyltin chloride, as disclosed in U.S. Pat. Nos. 4,519,431, 4,540,744, 4,603,722, 5,248,722, 5,349,024, 5,502,129, and 5,877,336, which are incorporated herein by reference. Other examples include cyclic amino compounds such as hexamethyleneimine alkyl chloride, as disclosed in U.S. Pat. Nos. 5,786,441, 5,916,976 and 5,552,473, which are incorporated herein by reference. Other examples include N-substituted aminoketones, N-substituted thioaminoketones, N-substituted aminoaldehydes, and N-substituted thioaminoaldehydes, including N-methyl-2-perrolidone or dimethylimidazolidinone (i.e., 1,3-dimethylethyleneurea) as disclosed in U.S. Pat. Nos. 4,677,165, 5,219,942, 5,902,856, 4,616,069, 4,929,679, 5,115,035, and 6,359,167, which are incorporated herein by reference. Additional examples include sulfur-containing or oxygen containing azaheterocycles such as disclosed in WO 2004/020475, U.S. Ser. No. 60/644,164 and U.S. Pat. No. 6,596,798, which are incorporated herein by reference. Other examples include boron-containing terminators such as disclosed in U.S. Ser. No. 60/591,065, which is incorporated herein by reference. Still other examples include cyclic siloxanes such as hexamethylcyclotrisiloxane, including those disclosed in copending U.S. Ser. No. 60/622,188, which is incorporated herein by reference. Further, other examples include α-halo-ω-amino alkanes, such as 1-(3-bromopropyl)-2,2,5,5-tetramethyl-1-aza-2,5-disilacyclopentane, including those disclosed in copending U.S. Ser. Nos. 60/624,347 and 60/643,653, which are incorporated herein by reference.

Useful coupling agents that can be employed in combination with the functionalizing agent include any of those coupling agents known in the art including, but not limited to, tin tetrachloride, tetraethyl ortho silicate, tetraethoxy tin, silicon tetrachloride, and mixtures thereof. In certain embodiments, the functionalizing agent can be employed in combination with other coupling or terminating agents. The combination of functionalizing agent with other terminating agent or coupling agent can be in any molar ratio.

In one embodiment, the functionalizing agent may be added to the living polymer cement (i.e., polymer and solvent) once a peak polymerization temperature, which is indicative of nearly complete monomer conversion, is observed. Because live ends may self-terminate, the functionalizing agent may be added within about 25 to 35 minutes of the peak polymerization temperature.

The amount of functionalizing agent employed to prepare the functionalized polymers is best described with respect to the equivalents of lithium or metal cation associated with the initiator. For example, the moles of functionalizing agent per mole of lithium may be about 0.3 to about 2, in other embodiments from about 0.6 to about 1.5, in other embodiments from about 0.7 to about 1.3, in other embodiments from about 0.8 to about 1.1, and in other embodiments from about 0.9 to about 1.0.

After formation of the polymer, a processing aid and other optional additives such as oil can be added to the polymer cement. The polymer and other optional ingredients may then be isolated from the solvent and optionally dried. Conventional procedures for desolventization and drying may be employed. In one embodiment, the polymer may be isolated from the solvent by steam desolventization or hot water coagulation of the solvent followed by filtration. Residual solvent may be removed by using conventional drying techniques such as oven drying or drum drying. Alternatively, the cement may be directly drum dried.

In one or more embodiments, the use of the initiator compounds of the present invention to anionically polymerize monomer can lead to the formation of functionalized polymers. In other words, polymers bearing a residue of the initiator compounds of the present invention can be formed, where the residue is located at the head of the polymer (i.e., at the location where the polymer chain was first propagated). In one or embodiments, these polymers may include high molecular weight polymers. In one or more embodiments, the weight average molecular weight ($M_w$) of the polymers may be in excess of 50 kg/mole, in other embodiments in excess of 100 kg/mole, in other embodiments in excess of 150 kg/mole, in other embodiments in excess of 200 kg/mole, and in other embodiments from about 50 to about 400 kg/mole. In these or other embodiments, the polymers may have a number average molecular weight ($M_n$) of the polymers may be in excess of 40 kg/mole, in other embodiments in excess of 80 kg/mole, in other embodiments in excess of 120 kg/mole, in other embodiments in excess of 180 kg/mole, and in other embodiments in from about 40 to about 300 kg/mole in. In these or other embodiments, the polymers may have a molecular weight distribution ($M_w/M_n$) of less than 2.0, in other embodiments less than 1.5, in other embodiments less than 1.3, in other embodiments less than 1.2, in other embodiments less than 1.1, and in other embodiments less than 1.0.

The functionalized polymers of one or more embodiments may be defined by the formula

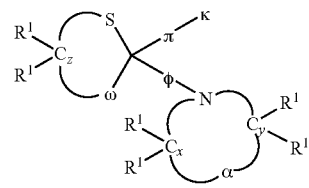

where π includes a polymer chain, κ is a hydrogen atom or a functional group resulting from termination with a functionalizing agent, and where each $R^1$, ω, α, φ, x, y, and z are defined as above.

The functionalized polymers of this invention are particularly useful in preparing tire components. These tire components can be prepared by using the functionalized polymers of this invention alone or together with other rubbery polymers. Other rubbery elastomers that may be used include natural and synthetic elastomers. The synthetic elastomers typically derive from the polymerization of conjugated diene monomers. These conjugated diene monomers may be copolymerized with other monomers such as vinyl aromatic monomers. Other rubbery elastomers may derive from the polymerization of ethylene together with one or more α-olefins and optionally one or more diene monomers.

Useful rubbery elastomers include natural rubber, synthetic polyisoprene, polybutadiene, polyisobutylene-co-isoprene, neoprene, poly(ethylene-co-propylene), poly(styrene-co-butadiene), poly(styrene-co-isoprene), and poly(styrene-co-isoprene-co-butadiene), poly(isoprene-co-butadiene), poly(ethylene-co-propylene-co-diene), polysulfide rubber, acrylic rubber, urethane rubber, silicone rubber, epichlorohydrin rubber, and mixtures thereof. These elastomers can have a myriad of macromolecular structures including linear, branched and star shaped. Other ingredients that are typically employed in rubber compounding may also be added.

The rubber compositions may include fillers such as inorganic and organic fillers. The organic fillers include carbon black and starch. The inorganic fillers may include silica, aluminum hydroxide, magnesium hydroxide, clays (hydrated aluminum silicates), and mixtures thereof.

A multitude of rubber curing agents may be employed, including sulfur or peroxide-based curing systems. Curing agents are described in 20 Kirk-Othmer, *Encyclopedia of Chemical Technology*, 365-468, (3$^{rd}$ Ed. 1982), particularly *Vulcanization Agents and Auxiliary Materials*, 390-402, and A. Y. Coran, *Vulcanization* in *Encyclopedia of Polymer Science and Engineering*, (2$^{nd}$ Ed. 1989), which are incorporated herein by reference. Vulcanizing agents may be used alone or in combination.

Other ingredients that may be employed include accelerators, oils, waxes, scorch inhibiting agents, processing aids, zinc oxide, tackifying resins, reinforcing resins, fatty acids such as stearic acid, peptizers, and one or more additional rubbers.

These stocks are useful for forming tire components such as treads, subtreads, black sidewalls, body ply skins, bead filler, and the like. Preferably, the functional polymers are employed in tread formulations. In one or more embodiments, these tread formulations may include from about 10 to about 100% by weight, in other embodiments from about 35 to about 90% by weight, and in other embodiments from about 50 to 80% by weight of the functional polymer based on the total weight of the rubber within the formulation. In one or more embodiments, the preparation of vulcanizable compositions and the construction and curing of the tire is not affected by the practice of this invention.

In one or more embodiments, the vulcanizable rubber composition may be prepared by forming an initial masterbatch that includes the rubber component and filler (the rubber component optionally including the functionalized polymer of this invention). This initial masterbatch may be mixed at a starting temperature of from about 25° C. to about 125° C. with a discharge temperature of about 135° C. to about 180° C. To prevent premature vulcanization (also known as scorch), this initial masterbatch may exclude vulcanizing agents. Once the initial masterbatch is processed, the vulcanizing agents may be introduced and blended into the initial masterbatch at low temperatures in a final mix stage, which preferably does not initiate the vulcanization process.

Optionally, additional mixing stages, sometimes called remills, can be employed between the masterbatch mix stage and the final mix stage. Various ingredients including the functionalized polymer of this invention can be added during these remills. Rubber compounding techniques and the additives employed therein are generally known as disclosed in Stephens, *The Compounding and Vulcanization of Rubber*, in *Rubber Technology* (2$^{nd}$ Ed. 1973).

The mixing conditions and procedures applicable to silica-filled tire formulations are also well known as described in U.S. Pat. Nos. 5,227,425, 5,719,207, 5,717,022, and European Patent No. 890,606, all of which are incorporated herein by reference. In one or more embodiments, where silica is employed as a filler (alone or in combination with other fillers), a coupling and/or shielding agent may be added to the rubber formulation during mixing. Useful coupling and shielding agents are disclosed in U.S. Pat. Nos. 3,842,111, 3,873,489, 3,978,103, 3,997,581, 4,002,594, 5,580,919, 5,583,245, 5,663,396, 5,674,932, 5,684,171, 5,684,172 5,696,197, 6,608,145, 6,667,362, 6,579,949, 6,590,017, 6,525,118, 6,342,552, and 6,683,135, which are incorporated herein by reference. In one embodiment, the initial masterbatch is prepared by including the functionalized polymer of this invention and silica in the substantial absence of coupling and shielding agents. It is believed that this procedure will enhance the opportunity that the functionalized polymer will react or interact with silica before competing with coupling or shielding agents, which can be added later curing remills.

Where the vulcanizable rubber compositions are employed in the manufacture of tires, these compositions can be processed into tire components according to ordinary tire manufacturing techniques including standard rubber shaping, molding and curing techniques. Typically, vulcanization is effected by heating the vulcanizable composition in a mold; e.g., it may be heated to about 140 to about 180° C. Cured or crosslinked rubber compositions may be referred to as vulcanizates, which generally contain three-dimensional polymeric networks that are thermoset. The other ingredients, such as processing aides and fillers, may be evenly dispersed throughout the vulcanized network. Pneumatic tires can be made as discussed in U.S. Pat. Nos. 5,866,171, 5,876,527, 5,931,211, and 5,971,046, which are incorporated herein by reference.

In order to demonstrate the practice of the present invention, the following examples have been prepared and tested. The examples should not, however, be viewed as limiting the scope of the invention. The claims will serve to define the invention.

EXAMPLES

Experiment I

2-[4-(4-methylpiperazino)]phenyl-1,3-dithiane was prepared by reacting 4-(4-methylpiperazino)benzaldehyde with 1,3-propanedithiol. Specifically, this dithiane was prepared as follows. To an oven-dried 500 ml flask fitted with a magnetic stirring bar and reflux condenser was introduced 9.0 g (44.05 mmol) of 4-(4-methylpiperazino)benzaldehyde, 17.0 g (88.5 mmol) of p-toluenesulfonic acid monohydrate, and 250 ml of THF. The mixture was stirred for 10 minutes, and then added 5.0 g of Montmorillonite KSF (clay supported sulfonic acid), followed by 5 ml (FW=108.23, d=1.078, 48.4 mmol) of 1,3-propanedithiol in 30 ml of THF. The mixture was refluxed under nitrogen for 20 hours. After cooling to room temperature, 12 ml of triethylamine (Et$_3$N) was added and stirred for 1 hour at room temperature, filtrated, the filtrate was washed with KOH (2N), saturated NaHCO$_3$ (2×100 ml), saturated NaCl (2×100 ml) and dried over MgSO$_4$ (anhydrous). The solvent was evaporated; the residue was chromatographed on silica gel (elution with hexane/EtOAc: 70/30 first, then hexane/EtOAc/Et$_3$N: 6030/10)] to yield 12.4 g (95.6%) of 2-[4(4-methylpiperazine)-phenyl]-1,3-dithiane as white solid. $^1$H-NMR (DCDI$_3$): δ 1.90 (m, 1H), 2.15 (m, 1H), 2.34, (s, 3H), 2.55 (t, J=5.0 Hz, 4H), 2.88 (m, 2H), 3.05 (m, 2H), 3.21 (t, J=5.1 Hz, 4H), 5.11 (s, 1H), 6.87 (m, 2H), 7.35 (m, 2H). $^{13}$C-NMR (CDCl$_3$): δ 25.01, 31.11 (2C), 46.14, 48.58 (2C), 50.75, 55.00 (2C), 115.75 (2C), 128.61 (2C), 129.80, 151.27.

Experiment II

Five distinct polymer samples were prepared by initiating the polymerization of butadiene and styrene with a lithiated dithiane initiator that was prepared by lithiating the dithiane compounds prepared in Experiment I in situ. Each polymer sample was terminated with a different terminating agent selected from (i) tributyltin chloride (TBTCl), (ii) 1,3-dimethyl-2-imidazolidinone (DMI), (iii) hexamethylcyclotrisiloxane (D$_3$), (iv) 1-(3-bromopropyl)-2,2,5,5-tetramethyl-1-aza-2,5-disilacyclopentane (PABr), and (v) isopropanol (i-PrOH).

Specifically, the polymer samples were prepared and isolated as follows. To a two gallon N$_2$ purged reactor equipped with a stirrer was added 2.176 kg of hexane, 0.330 kg of 33 weight percent styrene in hexane, and 1.979 kg of 22.0 weight percent butadiene in hexane. The reactor was then charged with a mixed solution of 1.54 g of 2-[4-(4-methylpiperazino) phenyl-1,3dithiane in 10 ml of THF and 1 ml of triethylamine with 3.0 ml of n-BuLi (1.54M) in hexane, and agitated at 24° C. for 5 minutes; then 0.9 ml of 1.6 M randomizer in hexane was charged, and the reactor jacket was then heated to 50° C. After about 26 minutes, the batch temperature peaked at 57.7° C. After an additional 25 minutes, the cement was removed from the reactor into the dried 28-oz glass bottles, terminated with tributyltin chloride (1.0 M in hexane, abbreviated as MPPDT-SBR-TBT), 1,3-dimethyl-2-imidazolidinone (DMI, 1.0 toluene, abbreviated as MPPDT-SBR-DMI), hexamethylcyclotrisiloxane (D$_3$, 1.46 M in hexane, abbreviated as MPPDT-SBR-D$_3$), 1-(3-bromopropyl)-2,2,5,5-tetramethyl-1-aza-2,5-disilacyclopentane (PABr, abbreviated as MPPDT-SBR-PA), and isopropanol (abbreviated as MPPDT-SBR-H) at 50° C. bath for 30 minutes, respectively, coagulated in isopropanol containing butylated hydroxy toluene (BHT), and drum dried to yield the polymer samples. The characteristics of the polymer samples are set forth in Tables II and IV.

Experiment III

A control polymer sample was prepared by initiating the polymerization of butadiene and styrene in a similar fashion to Experiment II except that n-butyllithium was employed without a dithiane. The characteristics of the resulting control polymer are set forth in Tables II and IV.

Experiment IV

The polymer samples synthesized above were employed to prepare vulcanizable rubber compositions, were cured, and were analyzed for various physical and dynamic properties. A first set of vulcanizable compositions were prepared with a "carbon black" recipe, which is set forth in Table I.

TABLE I

|  | Parts by weight |
| --- | --- |
| Stage 1 Ingredients |  |
| Polymer | 100 |
| Carbon Black-N343 type | 55 |
| Wax | 1 |
| Antioxidant | 0.95 |
| ZnO | 2.5 |
| Stearic Acid | 2 |
| Processing Oil | 10 |
| Stage 2 Ingredients |  |
| Sulfur | 1.3 |
| Accelerators | 1.9 |

A two-stage mixing procedure was employed to mix these compositions whereby all ingredients except the sulfur and accelerators were mixed in a first stage at an initial temperature of about 130° C. and a drop temperature of less than about 165° C. for about 5 minutes within a 65 g Brabender mixer operating initially at 60 rpm with necessary ramp-up in speed. After cooling, the remaining ingredients were added and mixed at 60° C. Samples of these mixtures were prepared into test samples and cured at 171° C. for 15 minutes. Those compositions prepared according to this recipe are designated with the letter "A." The physical and dynamic properties obtained from the analysis of the cured samples is set forth in Table II.

TABLE II

|  | Sample | | | | | |
| --- | --- | --- | --- | --- | --- | --- |
|  | 1A | 2A | 3A | 4A | 5A | 6A |
| Initiator: | BuLi | MPPDT-Li | MPPDT-Li | MPPDT-Li | MPPDT-Li | MPPDT-Li |
| Terminator: | i-PrOH | i-PrOH | TBTCl | DMI | PABr | D3 |
| M$_n$ | 112455 | 118515 | 116608 | 120028 | 150190 | 116847 |
| M$_w$/M$_n$ | 1.03 | 1.1 | 1.1 | 1.13 | 1.25 | 1.09 |
| % Coupling | 0.0 | 9.0 | 6.7 | 11.0 | 41.6 | 6.5 |
| T$_g$ (° C.) | −37.4 | −36.4 | −36.6 | −36.5 | −36.5 | −36.2 |
| ML$_{1+4}$ @ 130° C. | 26.3 | 32.2 | 45 | 46.5 | 72.5 | 31.1 |
| 300% Modulus @ 23° C. (MPa) | 10.6 | 12.11 | 15.11 | 14.65 | 14.92 | 12.58 |
| Tensile Strength @ 23° C. (MPa) | 16.66 | 18.48 | 17.43 | 20.61 | 20.44 | 17 |
| Temp Sweep 0° C. tan δ | 0.1908 | 0.1905 | 0.241 | 0.2277 | 0.2323 | 0.1931 |
| Temp Sweep 50° C. tan δ | 0.2632 | 0.237 | 0.1371 | 0.165 | 0.154 | 0.2267 |
| RDA 0.25-14% ΔG' (MPa) | 4.9274 | 3.3981 | 0.6732 | 0.7642 | 1.2535 | 3.8777 |
| 50° C. RDA Strain sweep (5% strain) tan δ | 0.2430 | 0.2000 | 0.0873 | 0.0886 | 0.1064 | 0.2018 |

TABLE II-continued

| | Sample | | | | | |
|---|---|---|---|---|---|---|
| | 1A | 2A | 3A | 4A | 5A | 6A |
| Bound Rubber (%) | 14.2 | 18.5 | 47.5 | 39.8 | 44.6 | 18.9 |
| 50° C. Dynastat tan δ | 0.2319 | 0.1853 | 0.0875 | 0.0842 | 0.1033 | 0.1898 |

Experiment V

Molecular weight was determined by employing a Waters Model 150-C GPC with THF as a solvent polystyrene standards. Mooney viscosity measurement was conducted at 130° C. using a large rotor. The Mooney viscosity was recorded as the torque when the rotor has rotated for 4 minutes. The sample is preheated at 130° C. for 1 minute before the rotor starts. The tensile mechanical properties were measured using the standard procedure described in the ASTM-D 412 at 25° C. and 100° C. The tensile test specimens had dumbbell shapes with a thickness of 1.9 mm. A specific gauge length of 25.4 mm is used for the tensile test. Bound rubber was determined by immersing small pieces of uncured stocks in a large excess of toluene for three days. The soluble rubber was extracted from the sample by the solvent. After three days, any excess toluene was drained off and the sample was air dried and then dried in an oven at approximately 100° C. to a constant weight. The remaining pieces form a weak coherent gel containing the filler and some of the original rubber. The amount of rubber remaining with the filler is the bound rubber. The bound rubber content is then calculated according to the following:

$$\% \text{ Bound Polymer} = \frac{100(W_d - F)}{R} \quad (1)$$

where $W_d$ is the weight of dried gel, F is the weight of filler in gel or solvent insoluble matter (same as weight of filler in original sample), and R is the weight of polymer in original sample. Percent coupling was determined by GPC.

Temperature sweep experiments were conducted with a frequency of 31.4 rad/sec using 0.5% strain for temperature ranging from −80° C. to 0° C., and 2% strain for the temperature ranging from 0° C. to 100° C. ΔG is the change in G' at 0.25% from G' at 14.00%. Payne effect (ΔG') data were obtained from the strain sweep experiment. A frequency of 6.28 rad/sec was used for strain sweep which is conducted at 50° C. with strain sweeping from 0.25% to 14.00%.

In a similar fashion to Experiment IV, a second set of vulcanizable compositions were prepared with a "carbon black silica" recipe, which is set forth Table III.

TABLE III

| | Parts by weight |
|---|---|
| Stage 1 Ingredients | |
| Polymer | 100 |
| Silica | 30 |
| Carbon Black | 35 |
| Antiozonant | 0.95 |
| Stearic Acid | 1.5 |
| LVA Oil | 10 |
| Stage 2 Ingredients | |
| 60% Active Silica Coupling Agent | 4.57 |
| Stage 3 Ingredients | |
| ZnO | 2.5 |
| Sulfur | 1.7 |
| Accelerator, CBS | 1.5 |
| PVI | 0.25 |
| Accelerator, DPG | 0.5 |

A three-stage mixing procedure was prepared to mix these compositions filler whereby all ingredients except the silica coupling agent, zinc oxide, sulfur, and accelerators were mixed at an initial temperature of 130° C. and a drop temperature below about 165° C. for 5 minutes within a 65 g Brabender mixer operating at an initial speed of 60 rpm with required ramp-up. In a second mixing stage, the silica coupling agent was added and the composition was mixed at 90° C. After cooling, the remaining ingredients were added and mixed at 60° C. Samples of these mixtures were prepared into test samples and cured at 171° C. for 25 minutes. Those compositions prepared according to this silica-containing recipe are designated with the letter "B."

TABLE IV

| | Sample | | | | | |
|---|---|---|---|---|---|---|
| | 1B | 2B | 3B | 4B | 5B | 6B |
| Initiator: | BuLi | MPPDT-Li | MPPDT-Li | MPPDT-Li | MPPDT-Li | MPPDT-Li |
| Terminator: | i-PrOH | i-PrOH | TBTCl | DMI | PABr | D3 |
| $M_n$ | 112455 | 118515 | 116608 | 120028 | 150190 | 116847 |
| $M_w/M_n$ | 1.03 | 1.1 | 1.1 | 1.13 | 1.25 | 1.09 |
| % Coupling | 0.0 | 9.0 | 6.7 | 11.0 | 41.6 | 6.5 |
| $T_g$ (° C.) | −37.4 | −36.4 | −36.6 | −36.5 | −36.5 | −36.2 |
| $ML_{1+4}$ @ 130° C. | 63.2 | 81.5 | 104.8 | 110.9 | 131.7 | — |
| 300% Modulus @ 23° C. (MPa) | 9.4 | 11.7 | 13.7 | 13.3 | 13.7 | 16.8 |
| Tensile Strength @ 23° C. (MPa) | 13 | 14.9 | 15 | 15.9 | 15.9 | 16.7 |
| Temp Sweep 0° C. tan δ | 0.1882 | 0.1851 | 0.2192 | 0.217 | 0.203 | 0.2595 |
| Temp Sweep 50° C. tan δ | 0.2407 | 0.2057 | 0.1622 | 0.1649 | 0.1661 | 0.146 |
| RDA 0.25-14% ΔG' (MPa) | 9.2 | 5 | 2.21 | 2.126 | 2.745 | 2.01 |

TABLE IV-continued

| | Sample | | | | | |
|---|---|---|---|---|---|---|
| | 1B | 2B | 3B | 4B | 5B | 6B |
| 50° C. RDA Strain sweep (5% strain) tan δ | 0.2260 | 0.1822 | 0.1233 | 0.1211 | 0.127 | 0.1188 |
| Bound Rubber (%) | 17.7 | 29.3 | 45.9 | 32.1 | 44.9 | 76.5 |
| 50° C. Dynastat tan δ | 0.22 | 0.1859 | 0.1274 | 0.1256 | 0.1247 | 0.1205 |

Various modifications and alterations that do not depart from the scope and spirit of this invention will become apparent to those skilled in the art. This invention is not to be duly limited to the illustrative embodiments set forth herein.

What is claimed is:

1. An initiator compound defined by the formula

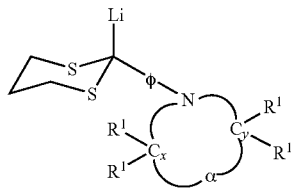

where φ includes an aryl or heteroaryl substituent, x is an integer from 1 to about 5, y is an integer from 1 to about 5, the sum of x and y is from about 3 to about 6, α is carbon, sulfur, oxygen, silicon, or an amino group, and each $R^1$ is individually hydrogen or a monovalent organic group or where two or more $R^1$ groups may join to form one or more rings.

2. The initiator compound of claim 1, where the aryl or heteroaryl substituent is selected from the group consisting of phenyl, thiophenyl, furanyl, n-methylpyrrolyl, thiazolyl, and pyridinyl groups.

3. A composition comprising:
an initiator compound defined by the formula

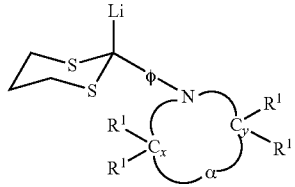

where φ includes an aryl or heteroaryl substituent, x is an integer from 1 to about 5, y is an integer from 1 to about 5, the sum of x and y is from about 3 to about 6, α is carbon, sulfur, oxygen, silicon, or an amino group, and each $R^1$ is individually hydrogen or a monovalent organic group or where two or more $R^1$ groups may join to form one or more rings.

4. The composition of claim 3, where the aryl or heteroaryl substituent is selected from the group consisting of phenyl, thiophenyl, furanyl, n-methylpyrrolyl, thiazolyl, and pyridinyl groups.

5. The composition of claim 3, wherein the solvent includes an aliphatic or cycloaliphatic solvent.

6. The composition of claim 5, where the aliphatic or cycloaliphatic solvent is selected from the group consisting of n-pentane, n-hexane, n-heptane, n-octane, n-nonane, n-decane, isopentane, isohexanes, isoheptanes, isooctanes, 2,2-dimethylbutane, petroleum ether, kerosene, petroleum spirits, cyclopentane, cyclohexane, methylcyclopentane, methylcyclohexane, or mixtures thereof.

7. The composition of claim 5, wherein the solvent further includes an ether solvent.

8. The composition of claim 7, wherein the solvent includes up to about 65 volume percent aliphatic or cycloaliphatic solvent.

9. The composition of claim 3, where the initiator compound is soluble and stable at room temperature and pressure for 24 hours within said solvent.

10. The composition of claim 9, where said solvent includes a mixture of solvents including up to 65 volume percent aliphatic or cycloaliphatic solvent with the remainder including and ether solvent.

11. A method of preparing a polymer by employing anionic polymerization techniques, the method comprising:
(i) providing monomer including conjugated dienes;
(ii) providing a polymerization medium including a nonpolar solvent;
(iii) providing an initiator solution including an initiator defined by the formula

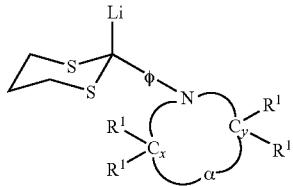

where φ includes an aryl or heteroaryl substituent, x is an integer from 1 to about 5, y is an integer from 1 to about 5, the sum of x and y is from about 3 to about 6, α is carbon, sulfur, oxygen, silicon, or an amino group, and each $R^1$ is individually hydrogen or a monovalent organic group or where two or more $R^1$ groups may join to form one or more rings; and
(iv) contacting the monomer and initiator within the polymerization medium.

12. The method of claim 11, where said monomer and initiator are contacted within the polymerization medium at a temperature of from about 20° to about 130° C.

13. The method of claim 11, where said step of contacting the monomer and initiator within the polymerization medium results in a living polymer, and further comprising the step of contacting the living polymer with a functionalizing agent.

14. The compound of claim 1, where the initiator compound is selected from the group consisting of 2-lithio-[4-(4-methylpiperazino)]phenyl-1,3-dithiane, and 2-lithio-[2-(4-methylpiperazino)]phenyl-1,3-dithiane.

15. The composition of claim 3, where the initiator compound is selected from the group consisting of 2-lithio-[4-(4- methylpiperazino)]phenyl-1,3-dithiane, and 2-lithio-[2-(4-methylpiperazino)]phenyl-1,3-dithiane.

16. The method of claim 11, where the initiator compound is selected from the group consisting of 2-lithio-[4-(4-methylpiperazino)]phenyl-1,3-dithiane, and 2-lithio-[2-(4-methylpiperazino)]phenyl-1,3-dithiane.

17. An initiator compound selected from the group consisting of 2-lithio-[4-(4-methylpiperazino)]phenyl-1,3-dithiane, 2-lithio-[2-(4-methylpiperazino)]phenyl-1,3-dithiane, 2-lithio-[2-morpholino]phenyl-1,3-dithiane, 2lithio-[4-morpholin-4-yl]phenyl-1,3-dithiane, 2-lithio-[2-morpholin-4-yl-pyridine-3]-1,3-dithiane, 2-lithio-[6-morpholin-4-pyridino-3]-1,3-dithiane, and 2-lithio-[4-methyl-3,4-dihydro-2H-1,4-benzoxazine-7]-1,3-dithiane.

18. A composition comprising the initiator of claim 17 and an aliphatic or cycloaliphatic solvent, where the composition includes at least 0.3 molar initiator compound and the solvent includes at least 65 volume percent aliphatic or cycloaliphatic solvent.

19. A method of preparing a polymer by employing anionic polymerization techniques, the method comprising:

(i) providing monomer including conjugated dienes;

(ii) providing a polymerization medium including a non-polar solvent;

(iii) providing an initiator solution including an initiator selected from the group consisting of 2-lithio-[4-(4-methylpiperazino)]phenyl-1,3-dithiane, 2-lithio-[2-(4-methylpiperazino)]phenyl-1,3-dithiane, 2-lithio-[2-morpholino]phenyl-1,3-dithiane, 2-lithio-[4-morpholin-4-yl]phenyl-1,3-dithiane, 2-lithio-[2-morpholin-4-yl-pyridine-3]-1,3-dithiane, 2-lithio-[6-morpholin-4-pyridino-3]-1,3-dithiane, and 2-lithio-[4-methyl-3,4-dihydro-2H-1,4-benzoxazine-7]-1,3-dithiane; and (iv) contacting the monomer and initiator within the polymerization medium.

* * * * *